United States Patent [19]

Shiba et al.

[11] Patent Number: 5,126,201
[45] Date of Patent: Jun. 30, 1992

[54] ABSORBENT ARTICLE

[75] Inventors: Daisuke Shiba; Norihiro Abe; Takatoshi Kobayashi, all of Tochigi, Japan

[73] Assignee: Kao Corporation, Tokyo, Japan

[21] Appl. No.: 458,063

[22] Filed: Dec. 28, 1989

[30] Foreign Application Priority Data

Dec. 28, 1988 [JP] Japan .................. 63-331628

[51] Int. Cl.$^5$ .............................................. D02G 3/00
[52] U.S. Cl. ...................... 428/389; 428/224; 428/288; 428/296; 428/372; 428/373; 428/374; 428/913
[58] Field of Search ............... 428/224, 373, 372, 374, 428/389, 913, 288, 296

[56] References Cited

U.S. PATENT DOCUMENTS

| | | | |
|---|---|---|---|
| 3,803,453 | 4/1974 | Hull | 317/2 R |
| 3,961,123 | 6/1976 | Ohtomo | 428/224 |
| 4,217,399 | 8/1980 | Dobo | 428/372 |
| 4,473,617 | 9/1984 | Van Leeuwen et al. | 428/372 |
| 4,522,868 | 6/1985 | Ohuchi et al. | 428/373 |
| 4,770,926 | 9/1988 | Yamamura et al. | 428/224 |

FOREIGN PATENT DOCUMENTS

| | | |
|---|---|---|
| 0002227 | 8/1979 | European Pat. Off. |
| 0070163 | 1/1983 | European Pat. Off. |
| 0072550 | 2/1983 | European Pat. Off. |
| 0162564 | 11/1985 | European Pat. Off. |
| 0276756 | 8/1988 | European Pat. Off. |
| 56-079717 | 6/1981 | Japan . |
| 59-207289 | 11/1984 | Japan . |
| 63-152413 | 6/1988 | Japan . |
| 1-306646 | 12/1989 | Japan . |
| 0925505 | 5/1963 | United Kingdom . |

*Primary Examiner*—George E. Lesmes
*Assistant Examiner*—Beverly A. Pawlikowski
*Attorney, Agent, or Firm*—Sughrue, Mion, Zinn Macpeak & Seas

[57] ABSTRACT

An absorbent article using, as a surface material (or a liquid-permeable top sheet), a nonwoven fabric is disclosed, the nonwoven fabric containing at least 10% by weight of a conjugate fiber comprising first and second parts differing from each other, wherein the second part covers at least a part of the first part, at least the first part contains an inorganic component in a proportion higher than that contained in the second part, and the content of the inorganic component in the first part is at least 1.5% by weight based on the weight of the first part. The nonwoven fabric has excellent cutting properties while retaining satisfactory strength, absorbency and touch.

9 Claims, No Drawings

ABSORBENT ARTICLE

FIELD OF THE INVENTION

This invention relates to a disposable absorbent article using, as a surface material, a nonwoven fabric excellent in absorbency and fabricability, which is particularly useful in sanitary napkins, baby's diapers, make-up sheets, etc.

BACKGROUND OF THE INVENTION

Conventional absorbent articles, such as sanitary napkins and paper diapers, basically comprise an absorbent layer composed of a fluffing pulp, absorbent paper, etc., a leakproof layer provided under and on the periphery of the absorbent layer, and a nonwoven fabric provided on the surface of the absorbent layer.

With the latest rapid developments of technology, new materials such as highly absorbent polymers and dry nonwoven fabrics have been introduced and have resulted in great improvements in the absorbing capacity of absorbent articles. In particular, synthetic fibers have been steadily extending their use as a material for nonwoven fabrics in place of the conventional widely used regenerated cellulose fibers because the nonwoven fabrics made therefrom are free from surface stickiness.

Despite their excellent absorbency, however, synthetic fibers give rise to increasing problems in the fabrication of a nonwoven fabric, particularly during cutting. Specifically, the cut area of a synthetic fiber nonwoven fabric suffers from considerable fluffing due to incompletely cut fibers, which gives not only an unfavorable appearance but also an uncomfortable touch. In extreme cases, the synthetic fiber nonwoven fabric cannot be made into a product because of a failure to cut the same.

The production of disposable absorbent articles such as sanitary napkins and paper diapers always involves cutting of products or materials. Cutting properties are considered to be related to the viscoelasticity of the fibers involved. In general, synthetic fibers are more liable to undergo plastic deformation than regenerated fibers and are therefore not easy to cut. Further, to reduce cost, it is required that the above described absorbent articles can be produced at high speed and cutting should be carried out in a short period of time. Cutting systems which can be so applied are limited. In particular, in a commonly employed cutting system using a metal blade, the durability or life of the blade greatly depends on the physical properties of materials to be cut, e.g., nonwoven fabrics. It is also undesirable for the nonwoven fabric to be roughly handled in cutting and, as a result, to sustain damage on parts other than cut areas.

A fundamental approach for improving cutting properties of synthetic fibers is to reduce the plastic deformability of the fibers so as to make them liable to brittle fracture. Means for realizing such an approach are of roughly divided two types.

One means is the incorporation of an inorganic powder component, e.g., titanium oxide and calcium carbonate, into a fiber forming resin so as to make the whole fiber brittle. This method is cheap and universally effective for any kind of resin. However, uniform distribution of an inorganic powder throughout the whole fiber as in conventional methods results in a serious problem of poor efficiency. That is, an effective improvement of cutting properties cannot be obtained unless an extremely large quantity of an inorganic component is added, and fiber properties tend to be deteriorated with the required extremely high content of the inorganic component. If the inorganic component content in the fiber constituting a nonwoven fabric for use as paper diapers or sanitary napkins is more than 1.0% by weight, the physical properties of the fiber in the neighborhood of its surface are considerably reduced. For example, in the case of hot melt binder fibers, the melt flow characteristics of the resin are impaired, resulting in reduced adhesion. In another case, the surface state of fibers which have been treated with a surface active agent, etc., changes to deteriorate various properties of the fibers, such as wettability.

An absorbent article using, as a surface material, a perforated sheet containing an opacifier such as titanium oxide is disclosed in JP-A-61-45753 (the term "JP-A" as used herein means an "unexamined published Japanese Patent Application") (corresponding to U.S. patent application Ser. No. 06/632,753). The absorbent article, by controlling the perforating ratio and the whiteness of the perforated sheet, has advantages such that passage of the liquid to be absorbed through the perforated sheet is improved and the appearance of the article is clean since the article is hardly seen. However, the cutting property of the perforated sheet, namely of the surface material of the absorbent article, is not improved.

Another means is control of the compounding components of the fiber-forming resins. From the fact that some high molecular weight resins have relatively high brittleness and are easy to cut, typically attempts have been made to increase the brittleness of the ultimate fibers by the blending of such resins. At the present, however, there are technical problems, such as a difficulty in deciding compounding of resins, and the narrow range of the resins which can be blended together. This has resulted in difficulty in reaching an industrially practical technique which can be economically practiced.

SUMMARY OF THE INVENTION

An object of this invention is to provide a nonwoven fabric which has sufficient cutting properties while satisfying the desired requirements of strength, absorbency and touch.

Another object of this invention is to provide an absorbent article using the above-described nonwoven fabric.

In order to obtain nonwoven fabrics having excellent cutting properties on a high speed line as well as satisfactory performance properties demanded in sanitary materials (e.g., sanitary napkins), i.e., adequate strength, absorption capacity and touch, it is required, as stated above, to reduce the plastic deformability of the fibers which constitute the nonwoven fabric without changing the surface physical properties of the fibers.

The inventors have studied the relationship between the site of a nonwoven fabric where an inorganic component is added and the relationship thereof to cutting properties. As a result, it has now been found that uniform distribution of an inorganic component throughout the whole fiber is unnecessary for achieving an improvement in cutting properties and that the objects of this invention are accomplished if a part of the fiber has a significantly reduced plastic deformability due to localization of an inorganic component.

The present invention relates to an absorbent article using, as a surface material (or a liquid-permeable top sheet), a nonwoven fabric containing at least 10% by weight of a conjugate fiber comprising first and second parts which differ from each other, based on the total weight of the nonwoven fiber, wherein the second part covers at least a part of the first part, at least the first part contains an inorganic component in a proportion higher than that contained in the second part, and the content of the inorganic component in the first part is at least 1.5% by weight based on the total weight of the first part.

DETAILED DESCRIPTION OF THE INVENTION

In the conjugate fiber of the present invention, it is preferred that the sectional area ratio of the second part is at least 20% of the total sectional area of the conjugate fiber.

The invention is illustrated by referring, for example, to a nonwoven fabric comprising hot melt binder fibers having a core/sheath structure comprising polypropylene as a core (first part) and polyethylene as a sheath (second part).

Comparing core/sheath fibers which uniformly contain titanium oxide or any other inorganic component having equal effects with those containing the same amount of the same inorganic component only in the core thereof, a nonwoven fabric made up of the latter fibers exhibits superior cutting properties. Further, in the latter case, the cutting properties are improved as the sectional are ratio of the core to the sheath becomes smaller, i.e., as the inorganic component content in the core is increased.

While incorporation of an inorganic component only into the core of a fiber has previously been proposed, such has only been for the purpose of providing a mat finish to the fibers and, in most cases, the content of the inorganic component in the whole fiber does not substantially exceed 0.5%, which yields no effect on cutting properties. According to the studies of the inventors, at least 1.5% by weight of an inorganic component based on the weight of the core is required for the fiber to have improved cutting properties and, preferably, at least 2.0% by weight is required for the fiber to have stable cutting suitability. On the other hand, if an inorganic component is uniformly added to the whole fiber in an amount of about 1.0% by weight based on the fiber, the physical properties of the surface or the whole of the second part are reduced. Taking, for example, the above specified core/sheath conjugate fiber whose sheath functions as a hot melt binder, the heat adhesion is reduced if both the core and sheath uniformly contain about 1.0% by weight of an inorganic component, whereas such adhesion reduction is not observed when the inorganic component is added only to the core. As another example, where the surface of a core/sheath conjugate fiber is rendered hydrophilic by a treatment with a surface active agent, the wettability of the fiber is reduced when the inorganic component is uniformly distributed throughout the fiber, whereas such a reduction in wettability is not observed when the inorganic component is present only in the core. Accordingly, where an inorganic component is incorporated also into the sheath, it is preferable that the content does not exceed 1.0% by weight based on the weight of the sheath so as to avoid a reduction in the fiber's physical properties. The minimum, of course, can be zero.

The methods for treating the surface of the nonwoven fabrics to impart hydrophilic property are described, for example, in JP-B-63-24416 (the term "JP-B" as used herein means an "examined Japanese Patent Publication")

Inorganic components which can be used in the present invention are not particularly limited and include an inorganic metallic salt such as titanium oxide, calcium carbonate and magnesium oxide. From the standpoint of workability in fiber manufacturing, titanium oxide is generally used.

The inorganic component is preferably incorporated into the conjugate fiber of the present invention in the powdery form.

Fibers constituting a nonwoven fabric which can be used as a surface material of an absorbent article according to the present invention are not limited to the above-described hot melt binder fibers. As long as the content of an inorganic component in the core and, if any, in the sheath falls within the above specified range, any other fibers are applicable to improve cutting properties while retaining the physical properties of the fiber surface.

Specific examples of suitable conjugate fibers (core/sheath) include polypropylene (PP)/polyethylene (PE) resins (inclusive of PE and ethylene copolymer resins), polyester resins [e.g., polyethylene terephthalate (PET), polybutylene terephthalate (PBT), or a blend thereof]/PE resins, polyamide resins (e.g., nylon 6, nylon 66)/PE resins, polyester resins/low-melting-point PET resins, and polyester resins/polyester resins. Among them, PP/PE resins, polyester resins/PE resins, polyester resins/low-melting-point polyester resins and polyester resins/polyester resins are preferred. PE resins include high density PE (HDPE), medium density PE (MDPE), low density PE (LDPE), super low density PE (SLDPE), and linear low density PE (LLDPE). Ethylene copolymer resins include an ethylene vinyl acetate copolymer (EVA), an ethylene ethyl acrylate copolymer (EEA), an ethylene acrylic acid copolymer (EAA), and ionomer resins. A blend of PE resins can also be used. A proper selection of materials of nonwoven fabric can be made from among these and any other resins.

The core of a fiber is not limited to one in number and may be divided into two or more sections. The cross sectional shape of the core is not limited to circular and may be irregular, such as a star and a cross. Further, the core may have a hollow structure or a porous structure. The sectional area ratio of the core/sheath preferably ranges from 80/20 to 20/80, more preferably from 60/40 to 40/60. Sufficient adhesion can hardly be obtained if it is more than 80/20, and sufficient cutting properties are hardly obtained if it is less than 20/80.

As stated above, the inorganic component may also be present in the sheath in such an amount that does not impair the physical properties at the vicinity of the fiber surface. It is desirable, however, that the inorganic component content in the sheath does not exceed 1.0% by weight based on the total weight of the sheath.

Methods of preparing the above mentioned conjugate fibers comprising two parts are described, for example, in *Senibinran Genrvo-hen* (Manual of fiber, Raw material), published by Maruzen Kabushikikaisya, page 889 (1978).

Methods of fabricating nonwoven fabrics of the conjuqate fibers comprising two parts, preferably fibers having a core/sheath structure, are not particularly restricted. Typically used methods include an air needling system, a water needling system or a needle punch system in which a fiber web is needled to provide a stable sheet; a binder bond system or a heat bond system in which fibers are bonded with a bonding agent or by self fusion of the fibers; a spun bond system in which filament fibers are sealed; and a wet method in which fibers are formed into a sheet by paper making technique. Nonwoven fabrics constructed by these methods usually have a single layer structure comprising a card web which is composed of the conjugate fibers of the present invention or a multi-layer structure comprising two or more of the card webs.

In order to improve the properties which are required for the nonwoven fabric such as strength of the fabric, the nonwoven fabric of the present invention may incorporates a fiber of a resin such as polyester resins in the card web of the conjugate fiber, or may be constructed a multi-layer structure comprising at least one layer of the card web of the conjugate fiber and at least one layer of the fibers of a resin such as polyester resins. However, it is essentially required that at least one layer contain the above described fibers having improved cutting properties. Desired effects are manifested so long as the nonwoven fabric contains at least 10% by weight, preferably from 40 to 100% by weight, of the above described fibers in terms of a mean value. Considering that the part prone to brittle fracture is preferably localized in a single fiber, it is also preferable that parts exhibiting satisfactory cutting properties be localized in a nonwoven fabric, which leads to an improvement in the cutting properties of the nonwoven fabric as a whole without causing a reduction in other physical properties. For example, where a nonwoven fabric has a multi-layer structure, only one or some of the plural layers need be constructed mainly of the fibers having the satisfactory cutting properties according to the desired nonwoven fabric characteristics.

The nonwoven fabric preferably has a basis weight of from 10 to 40 g/m² as a whole, with the basis weight of the surface layer thereof ranging from 5 to 15 g/m², for use as sanitary napkins; or from 15 to 50 g/m² as a whole, with the basis weight of the surface layer thereof ranging from 7 to 20 g/m², for use as paper diapers.

The conjugate fiber composed of the first and second parts usually has a fineness of from 1.5 to 10 denier and, in view of the strength touch balance, preferably of from 1.5 to 6 denier.

Since the thus obtained nonwoven fabric has a high reflectance due to the irregular reflection of the inorganic component, when it is used as a surface material of absorbent articles there is concomitantly produced the effect that the color of an absorbed colored liquid, e.g., blood or a loose feces, can be masked by the nonwoven fabric, thus reducing an uncomfortable visual reaction.

While the conjugate fibers composed of the first and second parts which can be used for making a nonwoven fabric include not only core/sheath fibers as above illustrated but also a side-by-side type and a sea-island type, the core/sheath structure is preferred from viewpoint of heat bond performance.

The present invention is now illustrated in greater detail by way of Examples, but it should be understood that the present invention is not to be construed as being limited thereto.

EXAMPLES 1 TO 22 AND COMPARATIVE EXAMPLES 1 TO 9

Table 1 below shows the composition of fibers according to the present invention and comparative fibers outside the scope of the present invention; the composition and physical properties of nonwoven fabrics made of these fibers; and the physical properties of absorbent articles using the nonwoven fabric as a surface material. Abbreviations in Table 1 have the following meanings.

| HDPE: | High density polyethylene |
|---|---|
| ImpPET: | Low melting polyester |
| PP: | Polypropylene |
| PET: | Polyester |
| Ny: | Nylon |

Preparation of Nonwoven Fabric

The nonwoven fabrics of Examples 1 through 18 and Comparative Examples 1 through 7 were produced by a heat bond system using the conjugate fibers as binder fibers in which hot air at 140° C. was passed through a card web to bond the conjugate fibers with other fibers by fusion. The fibers used in these examples had been treated with an alkyl phosphate type surface active agent so as to have a hydrophilic surface. The nonwoven fabrics of Examples 19 through 22 and Comparative Examples 8 and 9 were produced by needling a card web using a high-pressure water jet (jet pressure: 55 kg/cm²).

Preparation of Absorbent Articles

Absorbent articles were produced by removing a nonwoven fabric from a commercially available sanitary napkin "Lolie" (produced by Kao Corporation) and replacing the same with each of the nonwoven fabrics in Table 1 instead. Cutting was carried out as described below.

Method of Evaluations

1) Strength of Nonwoven Fabric

A 50 mm wide specimen of the nonwoven fabric (the fiber orientation direction was taken as a width direction) was held by chucks at a chuck distance of 150 mm, and the breaking strength at a pulling speed of 300 mm/min was measured.

2) Cutting Properties

An absorbent article was cut with a rotary die cutter while running at a speed of 30 m/min, and the cutting properties thereof were evaluated based on the following grading system.

3: Clear cut with no residual fibers on the cut area
2: Slight fluffing on the cut area
1 Significant fluffing on the cut area due to residual fiber 3) Hydrophilic Properties of Absorbent article A test liquid was dropped on the absorbent article tilted at 45° from a height of 1 cm, and the running distance of the liquid on the surface of the nonwoven fabric from the spot of dropping to the spot where the liquid was absorbed inside the absorbent article was measured and evaluated according to the following grading system. The shorter the distance, the higher the hydrophilic properties.

3: The liquid was absorbed at the instant of dropping.

2: After short running on the surface, the liquid was all absorbed.
1: The liquid ran down the surface and was not substantially absorbed.

4) Reflectance

Colorimetry was measured using a color difference meter "Model ND-101DP" (produced by Nippon Denshoku Kogyo K.K.). First, a correction was made so that the reflectance of a standard white board (barium sulfate) at a wavelength of 457 nm (green light) was 100%. Then, the reflectance of the surface material of the absorbent article was measured at the same wavelength and expressed as a percentage of the standard. For details of operations, reference can be made to the instructions for using Model ND-101DP.

TABLE 1

| | Nonwoven Fabric | | Fabric Composition | | | | Core/Sheath Sectional Area Ratio | Cutting Property | Strength (g) | Hydrophilic Properties | Reflectance (%) |
| | | | Core | | Sheath | | | | | | |
| | Composition | Fineness (denier) | Resin | TiO$_2$ Content (% by weight) | Resin | TiO$_2$ Content (% by weight) | | | | | |
| --- | --- | --- | --- | --- | --- | --- | --- | --- | --- | --- | --- |
| Comparative Example 1 | Fiber F(1) 100% | 2 | PP | 0.5 | HDPE | 0.0 | 50/50 | 1 | 646 | 3 | 15 |
| Comparative Example 2 | Fiber F(2) 100% | 2 | PP | 1.1 | HDPE | 0.0 | 50/50 | 1 | 622 | 3 | 21 |
| Example 1 | Fiber F(3) 100% | 2 | PP | 1.5 | HDPE | 0.0 | 50/50 | 2 | 653 | 3 | 27 |
| Example 2 | Fiber F(4) 100% | 2 | PP | 2.0 | HDPE | 0.0 | 50/50 | 3 | 630 | 3 | 30 |
| Example 3 | Fiber F(5) 100% | 2 | PP | 2.4 | HDPE | 0.0 | 50/50 | 3 | 636 | 3 | 32 |
| Example 4 | Fiber F(6) 100% | 2 | PP | 4.0 | HDPE | 0.0 | 50/50 | 3 | 621 | 3 | 39 |
| Example 5 | Fiber F(7) 100% | 2 | PP | 7.0 | HDPE | 0.0 | 50/50 | 3 | 643 | 3 | 44 |
| Example 6 | Fiber F(8) 100% | 2 | PP | 10.0 | HDPE | 0.0 | 50/50 | 3 | 632 | 3 | 51 |
| Example 7 | Fiber F(9) 100% | 2 | PP | 2.4 | HDPE | 0.0 | 70/30 | 3 | 589 | 3 | 38 |
| Example 8 | Fiber F(10) 100% | 2 | PP | 2.5 | HDPE | 0.0 | 40/60 | 3 | 711 | 3 | 29 |
| Example 9 | Fiber F(11) 100% | 2 | PP | 3.3 | HDPE | 0.0 | 30/70 | 3 | 749 | 3 | 28 |
| Example 10 | Fiber F(12) 100% | 2 | PP | 5.0 | HDPE | 0.0 | 20/80 | 3 | 790 | 3 | 26 |
| Comparative Example 3 | Fiber F(13) 100% | 2 | PP | 1.0 | HDPE | 0.5 | 50/50 | 1 | 600 | 2 | 23 |
| Comparative Example 4 | Fiber F(14) 100% | 2 | PP | 1.0 | HDPE | 1.0 | 50/50 | 1 | 551 | 1 | 25 |
| Comparative Example 5 | Fiber F(15) 100% | 2 | PP | 1.0 | HDPE | 2.0 | 50/50 | 2 | 493 | 1 | 27 |
| Comparative Example 6 | Fiber F(16) 100% | 2 | PP | 1.0 | HDPE | 2.0 | 70/30 | 2 | 470 | 1 | 34 |
| Example 11 | Fiber F(17) 100% | 3 | PET | 2.0 | HDPE | 0.0 | 50/50 | 3 | 633 | 3 | 31 |
| Example 12 | Fiber F(18) 100% | 3 | PET | 2.4 | HDPE | 0.0 | 50/50 | 3 | 640 | 3 | 36 |
| Example 13 | Fiber F(19) 100% | 3 | PET | 2.4 | HDPE | 0.0 | 70/30 | 2 | 607 | 3 | 41 |
| Example 14 | Fiber F(20) 100% | 3 | PET | 2.0 | ImpPET | 0.0 | 50/50 | 3 | 622 | 3 | 35 |
| Example 15 | Fiber F(21) 100% | 3 | PET | 2.4 | ImpPET | 0.0 | 50/50 | 3 | 631 | 3 | 38 |
| Example 16 | Fiber F(22) 100% | 3 | PET | 1.5 | ImpPET | 0.5 | 50/50 | 2 | 602 | 2 | 38 |
| Example 17 | Fiber F(23) 100% | 3 | PBT | 2.0 | ImpPET | 0.0 | 50/50 | 3 | 382 | 3 | 30 |
| Example 18 | Fiber F(24) 100% | 3 | Ny | 2.0 | ImpPET | 0.0 | 50/50 | 3 | 366 | 3 | 30 |
| Example 19 | Fiber F(25) 100% | 6 | PET | 2.0 | PET | 0.0 | 50/50 | 3 | 188 | 3 | 31 |
| Example 20 | Fiber F(26) 100% | 6 | PET | 2.4 | PET | 0.0 | 50/50 | 3 | 175 | 3 | 35 |
| Example 21 | Fiber F(27) 100% | 6 | PET | 1.5 | PET | 0.5 | 50/50 | 2 | 177 | 3 | 35 |
| Comparative Example 7 | Fiber F(28) 100% | 3 | PET | 0.5 | ImpPET | 0.0 | 50/50 | 1 | 371 | 3 | 14 |
| Comparative Example 8 | Fiber F(29) 100% | 6 | PET | 1.0 | ImpPET | 0.0 | 50/50 | 1 | 333 | 3 | 20 |
| Example 22 | Fiber F(4) | 2 | PP | 2.0 | HDPE | 0.0 | 50/50 | 3 | 427 | 3 | 32 |

TABLE 1-continued

| Nonwoven Fabric | | Fabric Composition | | | | Core/Sheath Sectional Area Ratio | Cutting Property | Strength (g) | Hydrophilic Properties | Reflectance (%) |
| --- | --- | --- | --- | --- | --- | --- | --- | --- | --- | --- |
| | | Core | | Sheath | | | | | | |
| Composition | Fineness (denier) | Resin | TiO$_2$ Content (% by weight) | Resin | TiO$_2$ Content (% by weight) | | | | | |
| 40% Fiber F(17) | 2 | PET | 2.0 | HDPE | 0.0 | 50/50 | | | | |
| 20% Fiber F(30) | 6 | — | — | PET | 1.0 | — | | | | |
| Comparative Example 9: 40% Fiber F(14) | 2 | PP | 1.0 | HDPE | 1.0 | 50/50 | 2 | 253 | 1 | 31 |
| 40% Fiber F(29) | 2 | PET | 1.0 | HDPE | 1.0 | 50/50 | | | | |
| 20% Fiber F(30) | 6 | — | — | PET | 1.0 | — | | | | |

It can be seen from the results of Table 1 that the nonwoven fabrics according to the present invention exhibited excellent cutting properties as well as a masking effect without suffering from a reduction of strength or hydrophilic properties.

To the contrary, the comparative samples of Comparative Examples 1 to 4, 7, and 8 showed no improvement in cutting properties because of a shortage of the inorganic component. The samples of Comparative Examples 5, 6, and 9, though exhibiting nearly satisfactory cutting properties, suffered from a serious reduction in nonwoven fabric strength and nonwoven fabric hydrophilic properties.

While the invention has been described in detail and with reference to specific embodiments thereof, it will be apparent to one skilled in the art that various changes and modifications can be made therein without departing from the spirit and scope thereof.

What is claimed is:

1. An absorbent article comprising, as a surface material, a nonwoven fabric containing at least 10% by weight of a conjugate fiber comprising first and second parts differing from each other, wherein said second part covers at least a part of said first part, at least said first part contains an inorganic component in a proportion higher than that contained in said second part, and the content of the inorganic component in said first part is at least 1.5% by weight based on the weight of said first part, wherein the inorganic component is titanium oxide, calcium carbonate, or magnesium oxide.

2. An absorbent article as claimed in claim 1, wherein said nonwoven fabric contains from 40 to 100% by eight of the conjugate fiber.

3. An absorbent article as claimed in claim 1, wherein said first part contains at least 2.0% by weight of said inorganic component.

4. An absorbent article as claimed in claim 1, wherein said second part contains not more than 1.0% by weight of said inorganic component.

5. An absorbent article as claimed in claim 1, wherein said conjugate fiber comprises a core and a sheath.

6. An absorbent article as claimed in claim 6, wherein a core to sheath cross sectional area ratio is from 80/20 to 20/80.

7. An absorbent article as claimed in claim 6, wherein a core to sheath cross sectional area ratio is from 60/40 to 40/60.

8. An absorbent article as claimed in claim 1, wherein said surface material is liquid permeable and wherein said first part improves the cutting properties of said non-woven fabric.

9. An absorbent article as claimed in claim 8, wherein said non-woven fabric has a surface which has been treated to render said surface hydrophilic.

* * * * *